United States Patent
Brotherton-Pleiss et al.

(10) Patent No.: US 9,388,172 B2
(45) Date of Patent: Jul. 12, 2016

(54) SUBSTITUTED CARBAMATE COMPOUNDS

(71) Applicant: Hoffmann-La Roche Inc., Little Falls, NJ (US)

(72) Inventors: Christine E. Brotherton-Pleiss, Sunnyvale, CA (US); Shawn David Erickson, Leonia, NJ (US); Hongju Li, Edison, NJ (US); Sung-Sau So, Verona, NJ (US)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/707,524

(22) Filed: May 8, 2015

(65) Prior Publication Data
US 2015/0239873 A1    Aug. 27, 2015

Related U.S. Application Data

(63) Continuation of application No. PCT/EP2013/073129, filed on Nov. 6, 2013.

(60) Provisional application No. 61/723,932, filed on Nov. 8, 2012.

(51) Int. Cl.
| C07D 413/14 | (2006.01) |
| C07D 413/06 | (2006.01) |
| C07D 403/06 | (2006.01) |
| C07D 401/06 | (2006.01) |
| C07D 271/107 | (2006.01) |

(52) U.S. Cl.
CPC .......... *C07D 413/06* (2013.01); *C07D 271/107* (2013.01); *C07D 401/06* (2013.01); *C07D 403/06* (2013.01); *C07D 413/14* (2013.01)

(58) Field of Classification Search
CPC ............. C07D 413/06; C07D 271/107; C07D 401/106; C07D 403/06; C07D 413/14
See application file for complete search history.

(56) References Cited

U.S. PATENT DOCUMENTS

2009/0105259 A1    4/2009   Jeong et al.

FOREIGN PATENT DOCUMENTS

| EP | 0903349 A2 | 3/1999 |
| WO | 01/98269 A2 | 12/2001 |
| WO | 2005/121100 A1 | 12/2005 |
| WO | 2008/124849 A2 | 10/2008 |
| WO | 2011/132017 A1 | 10/2011 |

OTHER PUBLICATIONS

Database CA [Online] Chemical Abstracts Service, Columbus, Ohio, US; Akhmedov, Sh. T. et al., "Synthesis and study of some morpholinoand chloropropyl carbamates", XP002717687, retrieved from STN Database accession No. 1982:85483; & Akhmedov, Sh. T. et al., "Synthesis and study of some morpholino- and chloropropyl carbamates", Izvestiya Vysshikh Uchebnykh Zavedenii, Khimiya I Khimicheskaya Tekhnologiya, 24(11), 1446-7 Coden: Ivukar; ISSN: 0579-2991, 1981, in 11 pages.
International Preliminary Report on Patentability issued in International Application No. PCT/EP2013/070999, dated Apr. 14, 2015, in 7 pages.
International Preliminary Report on Patentability issued in International Application No. PCT/EP2013/071402, dated Apr. 21, 2015, in 6 pages.
International Preliminary Report on Patentability issued in International Application No. PCT/EP2013/073129, dated May 12, 2015, in 6 pages.
International Search Report issued in International Application No. PCT/EP2013/070999, dated Jan. 1, 2014, in 4 pages.
International Search Report issued in International Application No. PCT/EP2013/071402, dated Nov. 22, 2013, in 4 pages.
International Search Report issued in International Application No. PCT/EP2013/073129, dated Dec. 11, 2013, in 3 pages.
Preti et al., "TRP channels as therapeutic targets in airway disorders: a patent review" Expert Opin. Ther. Patents 22(6):663-695 ( 2012).
Wang et al., "Synthesis and evaluation of 3-aryl piperidine analogs as potent and efficacious dopamine D4 receptor agonists" Bioorg. Med. Chem. 13:4667-4678 ( 2005).

*Primary Examiner* — Rebecca Anderson
(74) *Attorney, Agent, or Firm* — Lily J. Ackeman

(57) ABSTRACT

The invention is concerned with the compounds of formula (I):

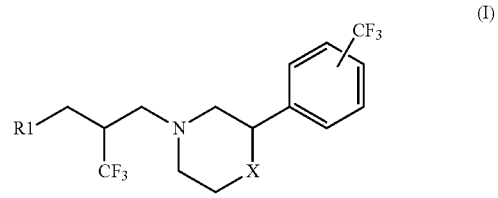

and pharmaceutically acceptable salts thereof. In addition, the present invention relates to methods of manufacturing and using the compounds of formula (I) as well as pharmaceutical compositions containing such compounds. The compounds of formula (I) are antagonists of the TRPA1 channel and may be useful in treating inflammatory diseases and disorders associated with that channel.

8 Claims, No Drawings

SUBSTITUTED CARBAMATE COMPOUNDS

CROSS REFERENCE TO RELATED APPLICATIONS

This application is a continuation of International Application No. PCT/EP2013/073129 having an international filing date of Nov. 6, 2013, the entire contents of which are incorporated herein by reference, and which claims benefit under 35 U.S.C. §119 to U.S. Provisional Patent Application No. 61/723,932 filed Nov. 8, 2012, the entire contents of which are incorporated herein by reference.

FIELD OF THE INVENTION

The present invention relates to organic compounds useful for therapy and/or prophylaxis in a mammal of an inflammatory disease or disorder, and in particular to substituted carbamate compounds, their manufacture, pharmaceutical compositions containing them and their use as Transient Receptor Potential (TRP) channel antagonists.

All documents cited to or relied upon below are expressly incorporated herein by reference.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor'. Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation.

SUMMARY OF THE INVENTION

The invention provides for a compound of formula (I):

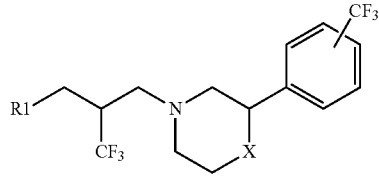

wherein:
X is —CH$_2$— or oxygen; and
R1 is benzoimidazolyl, benzimidazole ring substituted with a halogen, benzooxazolyl, benzooxazole ring substituted with a halogen, an unsubstituted 5-membered heteroaryl ring or a 5-membered heteroaryl ring substituted with halophenyl, methyl-pyridinyl or halo-pyridinyl, or a pharmaceutically acceptable salt thereof.

The invention also provides for pharmaceutical compositions comprising the compounds, methods of using the compounds and methods of preparing the compounds.

All documents cited to or relied upon below are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the R variables of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers". Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing equal proportions of the enantiomers is called a "racemic mixture". All such isomers, stereoisomers, enantiomers, chiral compounds and racemic mixtures fall within the scope of the invention described herein.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

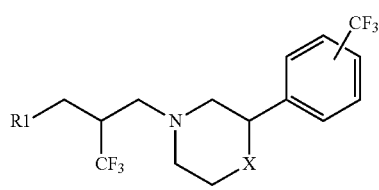

wherein:
X is —CH$_2$— or oxygen; and
R1 is benzoimidazolyl, benzimidazole ring substituted with a halogen, benzooxazolyl, benzooxazole ring substituted with a halogen, an unsubstituted 5-membered heteroaryl ring or a 5-membered heteroaryl ring substituted with halophenyl, methyl-pyridinyl or halo-pyridinyl, or a pharmaceutically acceptable salt thereof.

In another embodiment, the invention provides for compounds of formula (I) wherein X is —CH2-.

In another embodiment, the invention provides for compounds of formula (I) wherein X is carbon or oxygen.

In another embodiment, the invention provides for compounds of formula (I) wherein X is carbon.

In another embodiment, the invention provides for compounds of formula (I) wherein said 5-membered heteroaryl ring is imidazolyl, oxazolyl or oxadiazolyl.

In another embodiment, the invention provides for compounds of formula (I) wherein said halo moiety is fluorine or chlorine.

In another embodiment, the invention provides for compounds of formula (I) wherein the compound is:
5-Chloro-2-{3,3,3-trifluoro-2-[3-(3-trifluoromethylphenyl)-piperidin-1-ylmethyl]-propyl}-1H-benzoimidazole hydrochloride;
1-{2-[5-(4-Chlorophenyl)-1H-imidazol-2-ylmethyl]-3,3,3-trifluoropropyl}-3-(3-trifluoromethyl-phenyl)piperidine hydrochloride;
1-{2-[5-(4-Chlorophenyl)-[1,3,4]oxadiazol-2-ylmethyl]-3,3,3-trifluoropropyl}-3-(3-trifluoromethylphenyl)-piperidine hydrochloride;
6-Chloro-2-{3,3,3-trifluoro-2-[3-(3-trifluoromethylphenyl)-piperidin-1-ylmethyl]-propyl}-benzooxazole hydrochloride;
3-(3-Trifluoromethylphenyl)-1-[3,3,3-trifluoro-2-(5-phenyl-1H-imidazol-2-ylmethyl)-propyl]-piperidine hydrochloride;
1-{2-[5-(3-Chlorophenyl)-1H-imidazol-2-ylmethyl]-3,3,3-trifluoropropyl}-3-(3-trifluoromethyl-phenyl)piperidine hydrochloride;
1-{3,3,3-Trifluoro-2-[5-(4-fluorophenyl)-1H-imidazol-2-ylmethyl]-propyl}-3-(3-trifluoromethylphenyl)-piperidine hydrochloride;
1-{3,3,3-Trifluoro-2-[5-(4-fluorophenyl)-[1,3,4]oxadiazol-2-ylmethyl]-propyl}-3-(3-trifluoromethylphenyl)-piperidine hydrochloride;
1-{2-[5-(3-Chlorophenyl)-[1,3,4]oxadiazol-2-ylmethyl]-3,3,3-trifluoro-propyl}-3-(3-trifluoromethylphenyl)-piperidine hydrochloride;
2-Methyl-5-(5-{3,3,3-trifluoro-2-[3-(3-trifluoromethylphenyl)-piperidin-1-ylmethyl]-propyl}-[1,3,4]oxadiazol-2-yl)-pyridine;
5-Chloro-2-(5-{3,3,3-trifluoro-2-[3-(3-trifluoromethylphenyl)-piperidin-1-ylmethyl]-propyl}-[1,3,4]oxadiazol-2-yl)-pyridine hydrochloride;
4-{3,3,3-Trifluoro-2-[5-(4-fluoro-phenyl)-[1,3,4]oxadiazol-2-ylmethyl]-propyl}-2-(3-trifluoromethylphenyl)-morpholine hydrochloride;
1-{2-[5-(4-Chlorophenyl)-oxazol-2-ylmethyl]-3,3,3-trifluoro-propyl}-3-(3-trifluoromethyl-phenyl)-piperidine hydrochloride;
1-{2-[3-(4-Chlorophenyl)-[1,2,4]oxadiazol-5-ylmethyl]-3,3,3-trifluoropropyl}-3-(3-trifluoromethylphenyl)-piperidine hydrochloride;
1-{3,3,3-Trifluoro-2-[5-(4-fluoro-phenyl)-[1,2,4]oxadiazol-3-ylmethyl]-propyl}-3-(3-trifluoromethylphenyl)-piperidine hydrochloride;
4-{2-[5-(4-Chlorophenyl)-[1,3,4]oxadiazol-2-ylmethyl]-3,3,3-trifluoropropyl}-2-(3-trifluoromethylphenyl)-morpholine hydrochloride;
4-{3,3,3-Trifluoro-2-[5-(4-fluorophenyl)-[1,3,4]oxadiazol-2-ylmethyl]-propyl}-2-(4-trifluoromethylphenyl)-morpholine hydrochloride; or
4-{2-[5-(4-Chlorophenyl)-[1,3,4]oxadiazol-2-ylmethyl]-3,3,3-trifluoropropyl}-2-(4-trifluoromethylphenyl)-morpholinehydrochloride.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

In another embodiment, the invention provides for the use of a compound according to formula (I) for the preparation of a medicament for the treatment or prophylaxis of a respiratory disorder.

In another embodiment, the invention provides for a compound according to formula (I) for the treatment or prophylaxis of a respiratory disorder.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

Representative compounds of the invention have been shown to modulate TRPA1 activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, G1 tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (lBO), Crohn's disease, and ulcerative colitis (Geppetti, P. et al., *Br. J. Pharmacal.* 2004, 141, 1313-20; Yiangou, Y. et al., *Lancet* 2001, 357, 1338-39; Kimball, E. S. et al., *Neurogastroenterol. Motif.,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

In another specific embodiment, compounds of the invention can be administered to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neurpathic pain or inflammatory pain, comprising the step of administering a therapeutically effective amount of a compound according to formula (I) to a subject in need thereof.

In another embodiment, provided is an invention as hereinbefore described.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Schemes 1 below.

Scheme 1

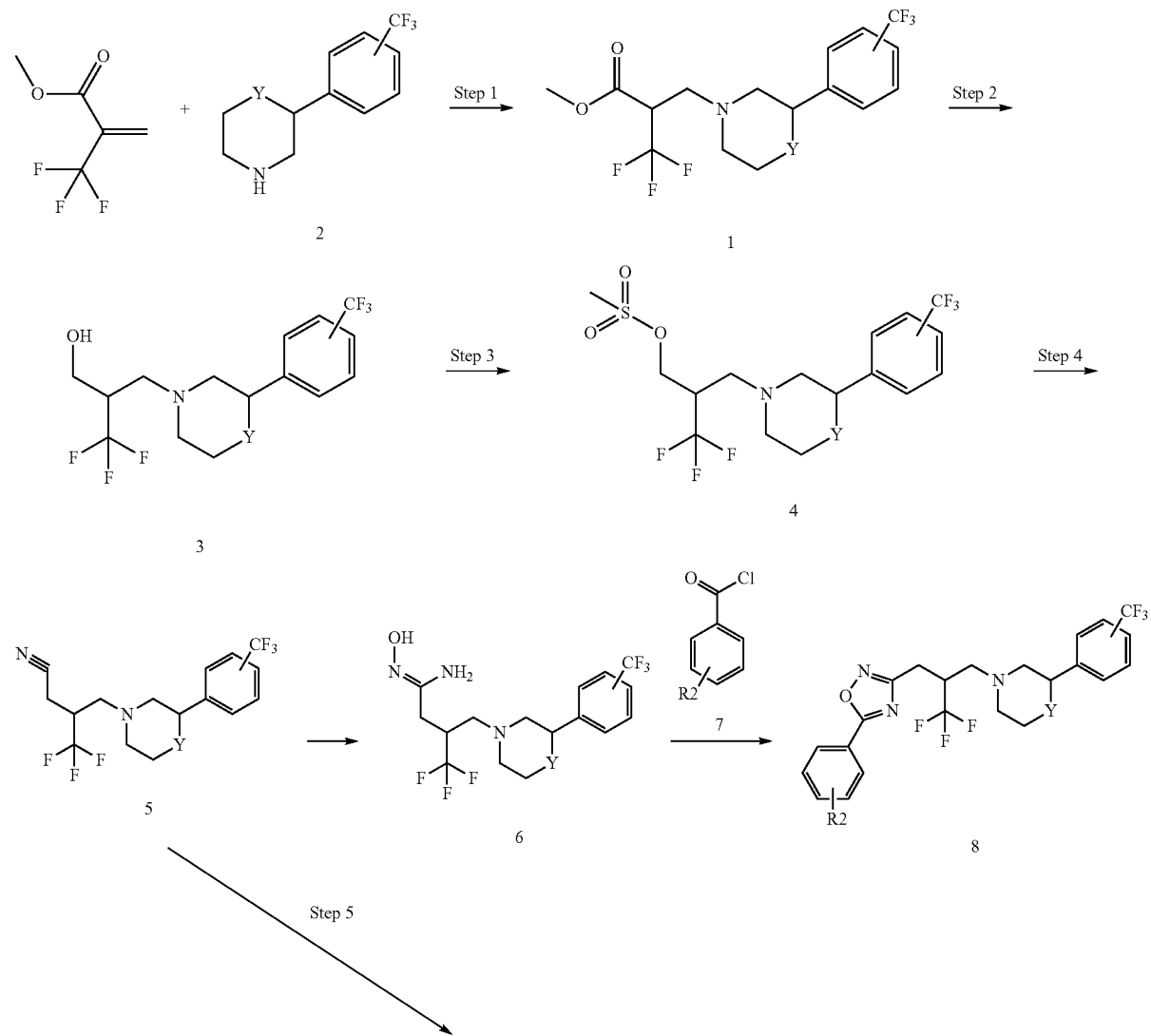

-continued

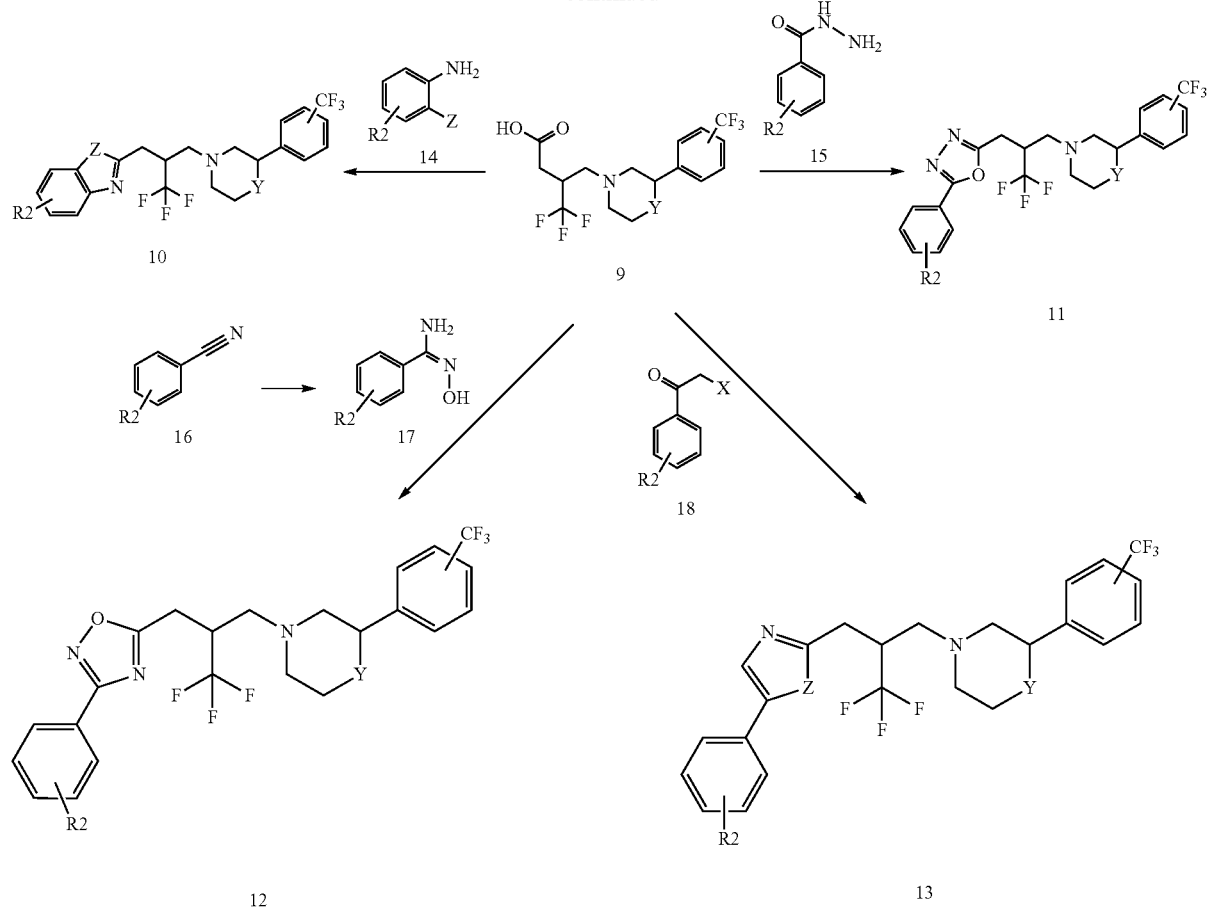

X = Br, NH$_2$
Y = CH$_2$, O
Z = N, O

According to Scheme 1, aminoester 1 can be prepared by reaction of a substituted morpholine or piperidine of formula 2 as a free base with 2-trifluoromethyl-acrylic acid methyl ester under standard Michael reaction conditions. This transformation is well-documented in the chemical literature and familiar to those skilled in the art. It proceeds under various reactions conditions, for example, the amine and the α,β-unsaturated ester can be combined in an aprotic solvent such as dichloromethane, tetrahydrofuran or acetonitrile or neat at room temperature or with heating. Starting 2-trifluoromethyl-acrylic acid methyl ester is commercially available. A large variety and number of substituted morpholines and substituted piperidines may be purchased from commercial sources or prepared by known procedures. Examples of commercially available cyclic amines include: 3-(3-trifluoromethylphenyl)-piperidine hydrochloride, 2-(3-trifluoromethyl-phenyl)-morpholine, 2-(3-trifluoromethyl-phenyl)-morpholine hydrochloride, and 2-[4-(trifluoromethyl)phenyl]morpholine oxalate. The intermediate ester 1 can then be reacted with a reducing agent such as lithium aluminum hydride, lithium borohydride or diisobutyl aluminum hydride to yield an alcohol intermediate of formula 3. This transformation is well-documented in the chemical literature and familiar to those skilled in the art. It proceeds under various reaction conditions, for example, the alcohol can be combined in a non-reducing solvent such as tetrahydrofuran, toluene, ether or dioxane and treated with a reducing agent such as lithium aluminum hydride. Intermediates of the general structure 3 can be converted to intermediate of formula 5 by well-established methods. For example, intermediate alcohol 3 can be combined in an aprotic solvent such as dichloromethane or dichloroethane and treated with a sulfonyl chloride such as methane sulfonyl chloride in the presence of a base such as diisopropylethylamine or triethylamine to give a sulfonate ester intermediate such as formula 4 which could be reacted with a cyanide source such as sodium cyanide, potassium cyanide, or tetra n-butylammonium cyanide in a solvent such as tetrahydrofuran, N,N-dimethylformamide, acetonitrile or DMSO to provide intermediates of formula 5. Intermediates of formula 5 can be combined with hydroxylamine or hydroxylamine hydrochloride by a variety of well-established methods to yield compounds of formula 6. This transformation is well-documented in the chemical literature and familiar to those skilled in the art. It proceeds under various reaction conditions, for example, a compound of formula 5 may be combined with hydroxylamine or hydroxylamine hydrochloride in a suitable solvent such as methanol, ethanol, isopropanol, water or mixture thereof, with or without an appropriate base such as hydroxide, carbonate or acetate or diisopropylethylamine at room temperature or with heating. The intermediate of formula 6 can be combined with substituted acid chlorides of formula 7 in an aprotic solvent such as dichloromethane with a suitable base such as diisopropylethylamine. The cyclodehydration of the resultant intermediate amide to form an oxadiazole of formula 8 may be carried out on the crude amide by evaporation and replacement of the solvent with a higher-boiling solvent such as N,N-dimethylformamide and the cyclization may be accomplished by heating (100-180° C.) conventionally or by microwave irradiation or by any other suitable known literature method.

Alternatively, the intermediate of formula 5 can be reacted under hydrolysis conditions to yield an intermediate of formula 9. This transformation is well-documented in the chemical literature and familiar to those skilled in the art. It proceeds under various reaction conditions, for example, the intermediate nitrile can be combined in a solvent such as ethanol or methanol with water or neat and heated in concentrated aqueous hydrochloric acid or alternatively the intermediate nitrile could be dissolved in a polar solvent such as ethanol, isopropanol, methanol, tetrahydrofuran, ethylene glycol or dioxane and treated with an aqueous base such as sodium hydroxide or potassium hydroxide.

Intermediate of formula 9 can be converted to heterocycles of formulas 10-13 by a variety of well-established methods [for example: Basu, S.; et al. *Bioorg. and Med. Chem. Letters* 2008, 18, 3695; Basu, S.; et al. *Bioorg. and Med. Chem. Letters* 2012, 22, 2843; Bessis, A-S.; et al. WO 2005-IB2390; Chan, W. N.; et al. US 2003-481083; Changkun, L.; et al.; *Bioorg. and Med. Chem. Letters* 2003, 13, 3817; Dickson, H. D. *Tetrahedron Lett.* 2009, 50, 6435; DiMauro, E. F.; et al. *Bioorg. and Med. Chem. Letters* 2008, 18, 4267; Dutta, M. M.; Goswami, B. N.; Kataky, J. C. S. *J. Heterocyclic Chemistry* 1984, 21, 1225; Edwards, L.; et al. US 2005-53752; Hobson, A. D.; et al. US 2006-875251P; Kangani, C. O.; Kelley, D. E.; Day, B. W. *Tetrahedron Lett.* 2006, 47, 6497; Kangani, C. O.; Day, B. W. *Tetrahedron Lett.* 2009, 50, 5332; Kaul, S; Kumar, A.; Sain, B. and Bhatnagar, A. K. *Syn. Comm.* 2007, 37, 2457; Liberatore, A-M.; et al. *Bioorg. and Med. Chem. Letters* 2004, 14, 3521; Adnan M. M.; et al.; US 2005-56498; Page, D. et al. *Bioorg. and Med. Chem. Letters* 2012, 22, 2843; Sharma, S.; et al. *Eur. J. Med. Chem.* 2009, 44, 1751; Stabile, P.; et al. *Tetrahedron Lett.* 2010, 51, 4801; Walter, M.; et al. *Bioorg. and Med. Chem. Letters* 2010, 20, 5883; Wen X.; et al. *Tetrahedron Lett.* 2012, 53, 2440; Wensbo, D.; et al. US 2002-402040P and references cited therein.]

For example, intermediates of formula 9 can be combined with benzene-1,2-diamines of formula 14 (Z=NH$_2$) by a variety of well-established methods to yield compounds of formula 10 (Z=NH). For example, the acid and benzene diamine can be combined in a solvent such as N,N-dimethylformamide, dichloromethane or acetonitrile and treated with any number of peptide coupling reagents such as 2-(1H-7-azabenzotriazol-1-yl)-1,1,3,3-tetramethyl uronium hexafluorophosphate methanaminium, bromo-tris-pyrrolidino phosphoniumhexafluorophosphate, O-(benzotriazol-1-yl)-N,N,N',N'-tetrametyluronium hexafluorophosphate, N-(3-dimethylaminopropyl)-N'-ethylcarbodiimide hydrochloride or dicyclohexyl carbodiimide with or without diisopropylethylamine and with or without 1-benztriazole to yield the amide which can undergo cyclodehydration by combining with an acid solution such as acetic acid or hydrochloric acid in dichloromethane or dichloroethane or boron trifluoride etherate in dioxane with heating to yield the benzimidazole of formula 10 (Z=NH) or alternatively intermediate 9 can be converted to intermediate 10 (Z=NH) by any other suitable known literature method. A variety and number of substituted benzene-1,2-diamine may be purchased from commercial sources or prepared by known procedures. Examples of commercially available benzene-1,2-diamines include: 4-chlorobenzene-1,2-diamine and 4-fluorobenzene-1,2-diamine.

Alternatively, intermediate of formula 9 can be combined with 2-aminophenols of formula 14 (Z=OH) by a variety of well-established methods to yield compounds of formula 10 (Z=O). For example, the carboxylic acid can be combined with a substituted aminophenol in an aprotic solvent such as toluene in the presence of an acid such a p-toluenesulfonic acid by heating with conventional heating or under microwave conditions or alternatively the carboxylic acid and the aminophenol can be combined in an aprotic solvent such as ethyl acetate and reacted with a reagent such as propylphosphonic anhydride with conventional heating or under microwave conditions to yield the benzoxazole of formula 10 (Z=O). A variety and number of substituted 2-aminophenols may be purchased from commercial sources or prepared by known procedures. Examples of commercially available 2-aminophenols include: 2-amino-5-chlorophenol and 2-amino-5-fluorophenol.

Alternatively intermediate of formula 9 can be combined with an aromatic acid hydrazide or a heteroaromatic acid hydrazide of formula 15 by a variety of well-established methods to yield compounds of formula 11. This transformation is well-documented in the chemical literature familiar to those skilled in the art. It proceeds under various reaction conditions, for example, an aromatic acid hydrazide or a heteroaromatic acid hydrazide can be combined with a carboxylic acid in a condensation solvent such as phosphorous oxychloride with heat. Alternatively, an aromatic acid hydrazide or a heteroaromatic acid hydrazide can be combined with a carboxylic acid with a coupling reagent such as propylphosphonic anhydride, 2-(1H-7-azabenzotriazol-1-yl)-1,1,3,3-tetramethyl uronium hexafluorophosphate methanaminium, bromo-tris-pyrrolidino phosphoniumhexafluorophosphate, O-(benzotriazol-1-yl)-N,N,N',N'-tetrametyluronium hexafluorophosphate, N-(3-dimethylaminopropyl)-N'-ethylcarbodiimide hydrochloride, N,N'-dicyclohexylcarbodiimide (DCC), or O-(benzotriazol-1-yl)-N,N,N',N'-tetraniethyluronium tetrafluoroborate (TBTU), and with bases such as diisopropylethylaniine and triethylamine ire solvents such as dichloromethane, tetrahydrofuran, or acetonitrile and then subsequently reacted under cyclodehydration conditions such as cyanuric chloride and indium in pyridine or Burgess reagent in a solvent such as O-tetrahydrofuran with a base such as diisopropylethylamine or p-toluene sulfonylchloride in a solvent such as acetonitrile, dichloromethane or acetone with a base such as potassium carbonate, triethylamine or diisopropylethylamine or by any other suitable known literature method. A variety and number of substituted aromatic acid hydrazides or heteroaromatic acid hydrazides may be purchased from commercial sources or prepared by known procedures. Examples of commercially available aromatic acid hydrazides and heteroaromatic acid hydrazides include: 4-chlorobenzhydrazide, 4-fluorobenzhydrazide, 3-chlorobenzhydrazide, 6-methylnicotinoyl hydrazide and 5-chloro-2-pyridinecarbohydrazide.

Alternatively, compound of formula 9 may be activated as follows: as the acid chloride formed from the acid using a suitable reagent such as oxalyl chloride or thionyl chloride; or alternatively as a anhydride or mixed anhydride formed from treatment with a reagent such as alkyl chloroformate in a suitable solvent such as tetrahydrofuran with a suitable base such as triethylamine; or alternatively using traditional methods to activate acids in amide coupling reactions such as EDCI with HOBT or uranium salts like HBTU or DCC with HOBT or HOAT with an appropriate base such as diisopropylethylamine in an appropriate solvent such as acetonitrile dioxane or N,N-dimethylformamide. This activated form of intermediate 9 may be combined with a compound of formula 17 to yield an intermediate ester. The cyclodehydration of this intermediate ester to form an oxadiazole of formula 12 may be carried out on the crude ester with evaporation and replacement of the solvent with a higher boiling solvent and the cyclization may be accomplished by heating conventionally or by microwave irradiation in a suitable solvent such as N,N-dimethylformamide (100-180° C.) or by any other suitable known literature method. A compound of formula 17 may be prepared from a suitable nitrile 16 by addition of hydroxylamine or hydroxylamine hydrochloride in a suitable solvent such as methanol, ethanol, water or mixture thereof, with or without an appropriate base such as hydroxide, carbonate or acetate. A variety and number of substituted aromatic acid nitriles may be purchased from commercial sources or prepared by known procedures. Examples of commercially available nitriles include: 4-chlorobenzonitrile, and 4-fluorbenzonitrile.

Alternatively, intermediate of formula 9 can be combined with aryl acyl bromides of formula 18 (X=Br) by a variety of well-established methods to yield compounds of formula 13 (Z=NH). For example, a carboxylic acid may be reacted with an aryl acyl bromide in the presence of base such as diisopropylethylamine, triethylamine, DBU, potassium carbonate or cesium carbonate in a polar solvent such as tetrahydrofuran or N,N-dimethyl formamide or methanol, ethanol, water or mixture thereof to afford an intermediate ketoester, which may be cyclized by heating conventionally or by microwave irradiation with an acetate salt such as ammonium acetate or sodium acetate in an appropriate high-boiling solvent such as acetic acid, N,N-dimethylformamide or xylene or a mixture thereof to yield an imidazole of formula 13 (Z=NH) or by any other suitable known literature method. A variety and number of substituted aryl acyl bromide may be purchased from commercial sources or prepared by known procedures. Examples of commercially available aryl acyl bromide include: 2-bromo-1-phenylethanone, 2-bromo-1-(4-chlorophenyl)ethanone, 2-bromo-1-(4-fluorophenyl)ethanone and 2-bromo-1-(3-chlorophenyl)ethanone.

Alternatively, intermediate of formula 9 can be combined with a substituted 2-aminoacetophenone or a salt thereof of formula 18 (X=NH$_2$) by a variety of well-established methods to yield compounds of formula 13 (Z=O). For example, the carboxylic acid and substituted 2-aminoacetophenone can be combined to form an intermediate amide which could undergo a cyclodehydration reaction to yield an oxazole of formula 13 (Z=O). This two-step procedure could be carried out as follows: In the first step, the substituted carboxylic acid could be combined with the substituted 2-aminoacetophenone or salt thereof in a solvent such as N,N-dimethylformamide, dichloromethane or acetonitrile and treated with any number of peptide coupling reagents such as 2-(1H-7-azabenzotriazol-1-yl)-1,1,3,3-tetramethyl uronium hexafluorophosphate methanaminium, bromo-tris-pyrrolidino phosphoniumhexafluorophosphate, O-(benzotriazol-1-yl)-N,N,N',N'-tetrametyluronium hexafluorophosphate, N-(3-dimethylaminopropyl)-N'-ethylcarbodiimide hydrochloride or dicyclohexyl carbodiimide with or without a base such as diisopropylethylamine or with or without 1-benztriazole to yield an intermediate amide. Alternatively in the first step, intermediate of formula 9 can be converted to the acid chloride using reagents such as oxalyl chloride or thionyl chloride in a solvent such as dichloromethane with N,N-dimethylformamide and then the intermediate acid chloride can be combined with the substituted 2-aminoacetophenone in a solvent such as dioxane or dichlormethane to yield the intermediate amide. In the second step this intermediate amide could undergo cyclodehydration by heating conventionally or by microwave irradiation with a dehydrating reagent such as POCl$_3$ or P$_2$O$_5$ neat or in a high-boiling solvent such as chloroform, toluene or xylene to yield an oxazole of formula 13 (Z=O) or by any other suitable known literature method. A variety and number of substituted 2-aminoacetophenones may be purchased from commercial sources or prepared by known procedures. Examples of commercially available substituted 2-aminoacetophenones include: 2-aminoacetophenone, 2-amino-4'-chloroacetophenone hydrochloride and 2-amino-4'-fluoroacetophenone hydrochloride.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep C$_{18}$ column (5 μm, OBD™ 20×100 mm) from Waters Corporation, or a SunFire™ Prep C$_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex®II FTICR with a 4.7 Tesla magnet (from Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

I. Preparation of Certain Intermediates

Intermediate A 4,4,4-trifluoro-3-((3-(3-(trifluoromethyl)phenyl)piperidin-1-yl)methyl)butanoic acid hydrochloride Step 1

In a 5 mL round-bottomed flask, 2-(3-(trifluoromethyl)phenyl)morpholine (650 mg, 2.81 mmol) was combined with methyl 2-(trifluoromethyl)acrylate (650 mg, 4.22 mmol; added slowly) to give a colorless solution and stirred at room temperature for 50 min. The crude reaction mixture was concentrated in vacuo to give an oil. The crude material was purified by flash chromatography (silica gel, 40+S, 0% to 30% ethyl acetate in hexanes) to afford 850 mg (78%)(methyl 3,3,3-trifluoro-2-((2-(3-(trifluoromethyl)phenyl)morpholino)-methyl)propanoate as a clear liquid. MH+=386.

Step 2

In a 20 mL pear-shaped flask, methyl 3,3,3-trifluoro-2-((2-(3-(trifluoromethyl)phenyl)morpholino)-methyl)propanoate (840 mg, 2.18 mmol) was combined with ether (30 ml) to give a colorless solution and cooled to 0° C. Lithium aluminum hydride (1.31 ml of a 2M solution in THF, 2.62 mmol) was added dropwise over 10 min and the reaction was stirred at 0° C. for 30 min and at room temperature for 20 min. The reaction mixture was cooled to 0° C., treated with $H_2O$ (0.5 ml), 2N aqueous NaOH (0.5 ml) and $H_2O$ (2 ml) and stirred for 20 min. The ethereal layer was washed with brine and $H_2O$, dried over $MgSO_4$, filtered and concentrated in vacuo to afford 760 mg (98%) of 3,3,3-trifluoro-2-[2-(3-trifluoromethyl-phenyl)-morpholin-4-ylmethyl]-propan-1-olanol as an oil. MH+=358.

Step 3

In a 50 mL round-bottomed flask, 3,3,3-trifluoro-2-((2-(3-(trifluoromethyl)phenyl)morpholino)-methyl)propan-1-ol (760 mg, 2.13 mmol) was combined with $CH_2Cl_2$ (10.0 ml) to give a colorless solution and then cooled to 0° C. DIPEA (412 mg, 557 µl, 3.19 mmol) and methanesulfonyl chloride (244 mg, 166 µl, 2.13 mmol) were added dropwise and the resulting reaction mixture was stirred for 30 min. The reaction was diluted with $CH_2Cl_2$ (30 ml), washed with sat. $NaHCO_3$ solution followed by washing with $H_2O$, dried over $MgSO_4$, filtered and concentrated to give 880 mg (95%) of methanesulfonic acid 3,3,3-trifluoro-2-[2-(3-trifluoromethyl-phenyl)-morpholin-4-ylmethyl]-propyl ester as a colorless oil. MH+=436.

Step 4

In a 20 mL round-bottomed flask, 3,3,3-trifluoro-2-((2-(3-(trifluoromethyl)phenyl)morpholino)-methyl)propyl methanesulfonate (850 mg, 1.95 mmol) and sodium cyanide (957 mg, 19.5 mmol) were combined with DMF (30 ml) to give a light yellow solution. The reaction mixture was heated at 60° C. and stirred for 2 h. The reaction mixture was diluted with ether (60 ml), washed with brine and $H_2O$, dried over $MgSO_4$, filtered and concentrated to give crude product as an oil. The crude material was purified by flash chromatography (silica gel, 40 g, 0% to 60% ethyl acetate in hexanes) to afford 400 mg (56%) of 4,4,4-trifluoro-3-[2-(3-trifluoromethylphenyl)-morpholin-4-ylmethyl]-butyronitrile as a colorless oil. MH+=367.

Step 5

4,4,4-Trifluoro-3-((2-(3-(trifluoromethyl)phenyl)morpholino)methyl)butanenitrile (100 mg, 273 µmol) was combined in 6N HCl solution and the reaction mixture was heated at 110° C. and stirred for 4 h. The reaction mixture was concentrated in vacuo to afford 100 mg (95%) of 4,4,4-trifluoro-3-[2-(3-trifluoromethyl-phenyl)-morpholin-4-ylmethyl]-butyric acid hydrochloride as a white foaming solid. MH+=386.

Intermediate B 4,4,4-Trifluoro-3-[3-(3-trifluoromethylphenyl)-piperidin-1-ylmethyl]butyronitrile 4,4,4-Trifluoro-3-[3-(3-trifluoromethylphenyl)-piperidin-1-ylmethyl]butyronitrile was prepared as a colorless oil by a similar procedure to Intermediate A (steps 1-4) except substituting 3-(3-trifluoromethylphenyl)-piperidine for 2-(3-(trifluoromethyl)phenyl)-morpholine in step 1. MH+=365.

II. Preparation of Certain Embodiments of the Invention

Example 1

5-Chloro-2-{3,3,3-trifluoro-2-[3-(3-trifluoromethyl-phenyl)-piperidin-1-ylmethyl]-propyl}-1H-benzoimidazole hydrochloride

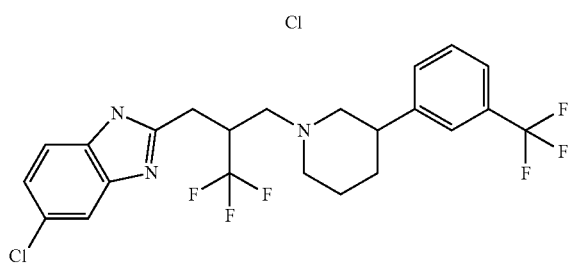 [SMILES: Cl ; FC(F)(F)c1cccc(C2CCCN(CC(Cc3nc4cc(Cl)ccc4[nH]3)C(F)(F)F)C2)c1]

Step 1

A mixture of 4.203 g (25 mmol) of ethyl 4,4,4-trifluorocrotonate, 20 mL of nitromethane and ca 0.576 g (5 mmol) of tetramethyl guanidine were stirred for 13 hours at room temperature, and then diluted with water and acidified by the addition of 0.5 M sulfuric acid. The mixture was extracted three times with diethyl ether. The combined ether extracts were washed with water, and then brine, dried over anhydrous sodium sulfate, filtered and concentrated under reduced pressure to give 5.601 g (98%) of 4,4,4-trifluoro-3-nitromethyl-butyric acid ethyl ester as an amber oil.

Step 2

In a 100 mL round-bottomed flask, KOH (356 mg, 5.45 mmol) was combined with $H_2O$ (50 ml) to give a colorless solution and cooled to 0° C. 4,4,4-Trifluoro-3-nitromethyl-butyric acid ethyl ester (1.25 g, 5.45 mmol) in 10 ml THF was added and the resulting reaction mixture was stirred for 20 min. This was followed by addition of $MgSO_4$ (657 mg, 5.45 mmol) in 5 ml of $H_2O$ then by $KMnO_4$ (862 mg, 5.45 mmol) in 30 ml of $H_2O$. The resulting reaction mixture was stirred for 30 min, filtered through celite and the celite cake washed with $CH_2Cl_2$. The combined filtrate and washes were washed with brine, dried over $Na_2SO_4$, filtered and concentrated to afford 4,4,4-trifluoro-3-formyl-butyric acid ethyl ester as a liquid which was used without purification.

Step 3

In a 200 mL round-bottomed flask, 4,4,4-trifluoro-3-formyl-butyric acid ethyl ester (260 mg, 1.31 mmol) and 3-(3-(trifluoromethyl)phenyl)piperidine (301 mg, 1.31 mmol) were combined with $CH_2Cl_2$ (20 ml) to give a colorless solution and cooled to 0° C. Acetic acid (158 mg, 150 µl, 2.62 mmol) was added followed by drop-wise addition of sodium triacetoxyborohydride (556 mg, 2.62 mmol) in 30 ml $CH_2Cl_2$. The resulting reaction mixture was stirred at room temperature overnight and then quenched with a saturated solution of $Na_2CO_3$ (30 ml). The organic layer was washed with brine and $H_2O$, dried wover $MgSO_4$, filtered and concentrated in vacuo to give a liquid which was purified on a silica column (hexane to 30% ethyl acetate/hexane) to afford 136 mg (25%) of ethyl ester as a clear liquid. MH+=412.

Step 4

In a 10 mL pear-shaped flask, 4,4,4-trifluoro-3-[3-(3-trifluoromethyl-phenyl)-piperidin-1-ylmethyl]-butyric acid ethyl ester (130 mg, 316 μmol) and NaOH (237 μl, 474 μmol) were combined with ethanol (6 ml) to give a colorless solution. The reaction mixture was heated at 90° C. and stirred for 30 min. The reaction mixture was concentrated and treated with a saturated solution of NaH$_2$PO$_4$ (20 ml) and extracted with ethyl acetate (2×30 ml). The combined organics were washed with brine and H$_2$O, dried over MgSO$_4$, filtered and concentrated to give 120 mg (99%) of 4,4,4-trifluoro-3-[3-(3-trifluoromethyl-phenyl)-piperidin-1-ylmethyl]-butyric acid as a waxy solid. MH+=384.

Step 5

In a 10 mL pear-shaped flask, 4,4,4-trifluoro-3-((3-(3-(trifluoromethyl)phenyl)piperidin-1-yl)methyl)butanoic acid (50 mg, 130 μmol, Eq: 1.00) and HATU (49.6 mg, 130 μmol, Eq: 1.00) were combined with DMF (2 ml) to give a colorless solution and stirred for 10 min. 4-chlorobenzene-1,2-diamine (18.6 mg, 130 μmol, Eq: 1.00) and DIPEA (50.6 mg, 68.3 μl, 391 μmol, Eq: 3) were added and stirred at room temperature for 1 hr. It was diluted with ethyl acetate (30 ml) and washed with brine and H$_2$O, dried with MgSO$_4$, filtered and concentrated in vacuo to give 65 mg (98%) of a mixture of N-(2-amino-4-chlorophenyl)-4,4,4-trifluoro-3-((3-(3-(trifluoromethyl)phenyl)piperidin-1-yl)methyl)butanamide and N-(2-amino-5-chlorophenyl)-4,4,4-trifluoro-3-((3-(3-(trifluoromethyl)phenyl)piperidin-1-yl)methyl)butanamide as a red viscous oil. MH+=508.

In a 5 mL pear-shaped flask, the above mixture (60 mg, 118 μmol) was combined with acetic acid (1000 mg, 953 μl, 16.7 mmol) to give a red solution. The reaction mixture was heated at 80° C. and stirred for 30 min. The crude reaction mixture was concentrated in vacuo, dissolved in ethyl acetate (30 ml), washed with a solution of saturated Na$_2$CO$_3$ and H$_2$O. The organic layer was dried over MgSO$_4$, filtered, concentrated and then purified on a silica column (CH$_2$Cl$_2$ to 30% ethyl acetate/CH$_2$Cl$_2$ eluent) to afford 5-chloro-2-{3,3,3-trifluoro-2-[3-(3-trifluoromethyl-phenyl)-piperidin-1-ylmethyl]-propyl}-1H-benzoimidazole as an oil. The oil was dissolved in ether and hexane. A solution of 4N HCl in dioxanes (0.15 ml) was added and the mixture was concentrated to afford 52 mg of 5-chloro-2-{3,3,3-trifluoro-2-[3-(3-trifluoromethyl-phenyl)-piperidin-1-ylmethyl]-propyl}-1H-benzoimidazole hydrochloride as an off white solid. MH+=490.

Example 2

1-{2-[5-(4-Chloro-phenyl)-1H-imidazol-2-ylmethyl]-3,3,3-trifluoro-propyl}-3-(3-trifluoromethyl-phenyl) piperidine hydrochloride

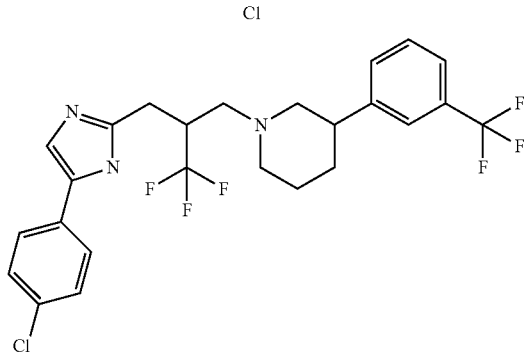 [SMILES: Cl ; FC(F)(F)c1cccc(C2CCCN(CC(Cc3ncc(-c4ccc(Cl)cc4)[nH]3)C(F)(F)F)C2)c1]

In a 10 mL pear-shaped flask, 4,4,4-trifluoro-3-((3-(3-(trifluoromethyl)phenyl)piperidin-1-yl)methyl)butanoic acid (50 mg, 130 μmol) and DIPEA (50.6 mg, 68.3 μl, 391 μmol) were combined with DMF (2 ml) to give a colorless solution. 2-Bromo-1-(4-chlorophenyl)ethanone (60.9 mg, 261 μmol) was added and the resultant mixture was stirred at room temperature overnight. The reaction was diluted with ethyl acetate, washed with brine and H$_2$O, dried with MgSO$_4$, filtered and concentrated. The crude residue was purified on a silica column (100% hexane to 30% ethyl acetate/hexane eluent) to afford 54 mg (77%) of 2-(4-chlorophenyl)-2-oxoethyl 4,4,4-trifluoro-3-((3-(3-(trifluoromethyl)-phenyl)piperidin-1-yl)methyl)butanoate as an oil. MH+=536.

To a 5 mL microwave vial was added 2-(4-chlorophenyl)-2-oxoethyl 4,4,4-trifluoro-3-((3-(3-(trifluoromethyl)phenyl)piperidin-1-yl)methyl)butanoate (20 mg, 37.3 μmol), ammonium acetate (57.5 mg, 746 μmol) and acetic acid (1.5 ml). The vial was capped and heated in the microwave at 120° C. for 30 min. It was concentrated to remove acetic acid, diluted with ethyl acetate (15 ml), washed with saturated Na$_2$CO$_3$ solution and H$_2$O, dried over MgSO$_4$, filtered and concentrated to give an oil. The oil was purified on a silica column (100% CH$_2$Cl$_2$ to 40% ethyl acetate/CH$_2$Cl$_2$ eluent) to afford an oil which was dissolved in ether/hexane (1 ml/1 ml). A 4N HCl solution in dioxanes (3 drops) was added and the mixture was concentrated to afford 8 mg (39%) of 1-{2-[5-(4-chlorophenyl)-1H-imidazol-2-ylmethyl]-3,3,3-trifluoro-propyl}-3-(3-trifluoromethyl-phenyl)piperidine hydrochloride as a solid. MH+=516.

Example 3

1-{2-[5-(4-Chloro-phenyl)-[1,3,4]oxadiazol-2-ylmethyl]-3,3,3-trifluoro-propyl}-3-(3-trifluoromethyl-phenyl)-piperidine hydrochloride

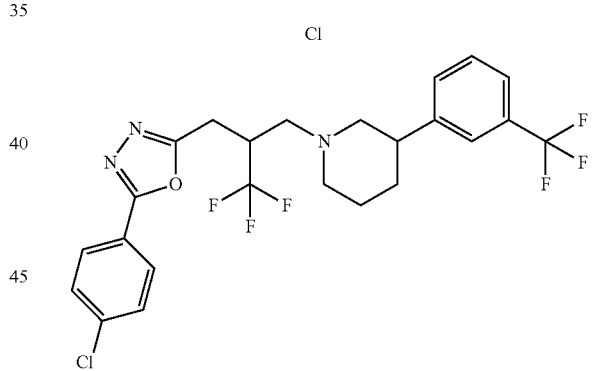

To a round-bottomed flask (5 ml) was added 4,4,4-trifluoro-3-((3-(3-(trifluoromethyl)phenyl)-piperidin-1-yl)methyl)butanoic acid (50 mg, 130 μmol), 4-chlorobenzohydrazide (22.3 mg, 130 μmol,) and POCl$_3$ (1.64 g, 1 mL, 10.7 mmol). The reaction mixture was heated to reflux at 110° C. for 4 hr. The crude reaction mixture was allowed to cool to room temperature, poured into ice/water and made basic with a saturated solution of Na$_2$CO$_3$. The reaction mixture was extracted with ethyl acetate, washed with brine and H$_2$O, dried over MgSO$_4$, filtered and concentrated. The resultant residue was purified on a silica column (100% CH$_2$Cl$_2$ to 40% ethyl acetate/CH$_2$Cl$_2$ eluent) to give an oil. The oil was dissolved in ether/hexane, treated with 4N HCl in dioxane (0.2 ml) and concentrated to afford 40 mg (56%) of 1-{2-[5-(4-chloro-phenyl)-[1,3,4]oxadiazol-2-ylmethyl]-3,3,3-trifluoro-propyl}-3-(3-trifluoromethyl-phenyl)-piperidine hydrochloride as a white solid. MH+=518.

Example 4

6-Chloro-2-{3,3,3-trifluoro-2-[3-(3-trifluoromethyl-phenyl)-piperidin-1-ylmethyl]-propyl}-benzooxazole hydrochloride

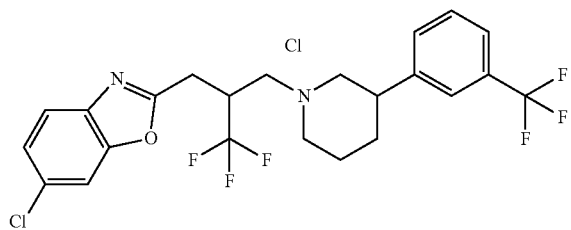 [SMILES: FC(F)(F)c1cccc(C2CCCN(CC(Cc3nc4ccc(Cl)cc4o3)C(F)(F)F)C2)c1 ; Cl]

In a 5 mL microwave vial, 4,4,4-trifluoro-3-((3-(3-(trifluoromethyl)phenyl)piperidin-1-yl)methyl)butanoic acid (50 mg, 130 μmol), 2-amino-5-chlorophenol (28.1 mg, 196 μmol) and p-toluenesulfonic acid (4.96 mg, 26.1 μmol) were combined in toluene (1.00 ml) to give a dark brown suspension. The tube was sealed and heated in a microwave at 135° C. for 2 h, diluted with ethyl acetate (30 ml), washed with a saturated solution of Na$_2$CO$_3$ (30 ml) and H$_2$O (30 ml), dried over MgSO$_4$, filtered and concentrated in vacuo to give an oil. The oil was purified on a silica column (100% CH$_2$Cl$_2$ to 50% ethyl acetate/CH$_2$Cl$_2$ gradient) to afford an oil which was dissolved in ether/hexane (1 ml/1 ml), treated with a 4N HCl solution in dioxanes (0.02 ml) and concentrated to afford 25 mg (37%) of 6-chloro-2-{3,3,3-trifluoro-2-[3-(3-trifluoromethyl-phenyl)-piperidin-1-ylmethyl]-propyl}-benzooxazole hydrochloride as a light red solid. MH+=491.

Example 5

3-(3-Trifluoromethyl-phenyl)-1-[3,3,3-trifluoro-2-(5-phenyl-1H-imidazol-2-ylmethyl)-propyl]-piperidine hydrochloride

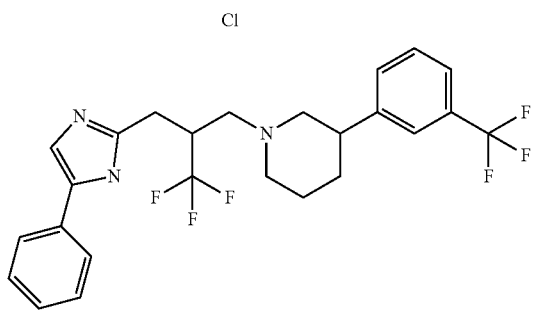 [SMILES: Cl ; FC(F)(F)c1cccc(C2CCCN(CC(Cc3ncc(-c4ccccc4)[nH]3)C(F)(F)F)C2)c1]

Prepared by a similar procedure to example 2 except substituting 2-bromo-1-phenylethanone for 2-bromo-1-(4-chlorophenyl)ethanone afforded 15 mg of 3-(3-trifluoromethyl-phenyl)-1-[3,3,3-trifluoro-2-(5-phenyl-1H-imidazol-2-ylmethyl)-propyl]-piperidine hydrochloride as an off-white solid. LCMS MH+=482.

Example 6

1-{2-[5-(3-Chlorophenyl)-1H-imidazol-2-ylmethyl]-3,3,3-trifluoro-propyl}-3-(3-trifluoromethyl-phenyl)piperidine hydrochloride

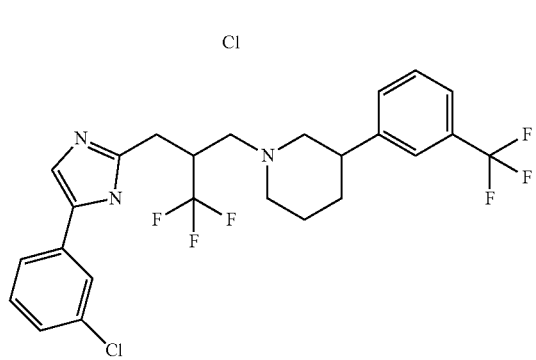 [SMILES: Cl ; FC(F)(F)c1cccc(C2CCCN(CC(Cc3ncc(-c4cccc(Cl)c4)[nH]3)C(F)(F)F)C2)c1]

Prepared by a similar procedure to example 2 except substituting 2-bromo-1-(3-chlorophenyl)ethanone for 2-bromo-1-(4-chlorophenyl)ethanone afforded 12 mg of 1-{2-[5-(3-chlorophenyl)-1H-imidazol-2-ylmethyl]-3,3,3-trifluoro-propyl}-3-(3-trifluoromethyl-phenyl)piperidine hydrochloride as an off-white solid. LCMS MH+=516.

Example 7

1-{3,3,3-Trifluoro-2-[5-(4-fluoro-phenyl)-1H-imidazol-2-ylmethyl]-propyl}-3-(3-trifluoromethyl-phenyl)-piperidine hydrochloride

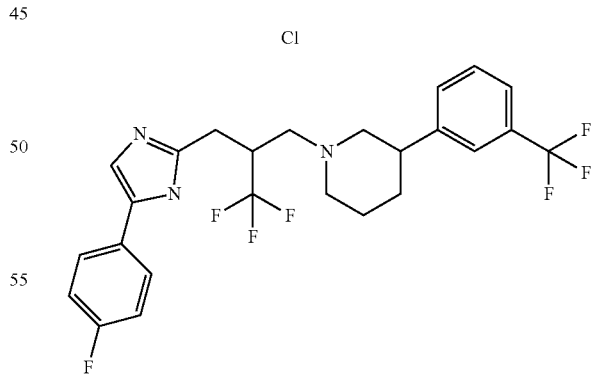

Prepared by a similar procedure to example 2 except substituting 2-bromo-1-(4-fluorophenyl)ethanone for 2-bromo-1-(4-chlorophenyl)ethanone afforded 9 mg of 1-{3,3,3-trifluoro-2-[5-(4-fluorophenyl)-1H-imidazol-2-ylmethyl]-propyl}-3-(3-trifluoromethyl-phenyl)-piperidine hydrochloride as an off-white solid. LCMS MH+=500.

Example 8

1-{3,3,3-Trifluoro-2-[5-(4-fluorophenyl)-[1,3,4]oxadiazol-2-ylmethyl]-propyl}-3-(3-trifluoromethyl-phenyl)-piperidine hydrochloride

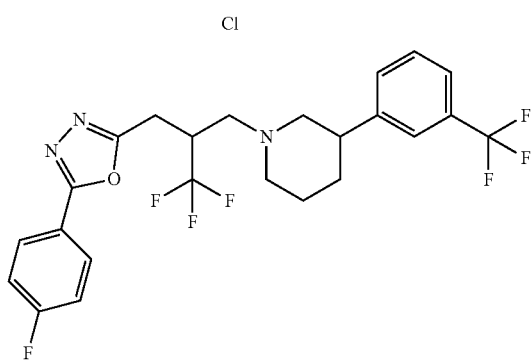

Prepared by a similar procedure to example 3 except substituting 4-fluorobenzohydrazide for 4-chlorobenzohydrazide afforded 58 mg of 1-{3,3,3-trifluoro-2-[5-(4-fluorophenyl)-[1,3,4]oxadiazol-2-ylmethyl]-propyl}-3-(3-trifluoromethyl-phenyl)-piperidine hydrochloride as a white solid. LCMS MH+=502.

Example 9

1-{2-[5-(3-Chloro-phenyl)-[1,3,4]oxadiazol-2-ylmethyl]-3,3,3-trifluoro-propyl}-3-(3-trifluoromethyl-phenyl)-piperidine hydrochloride

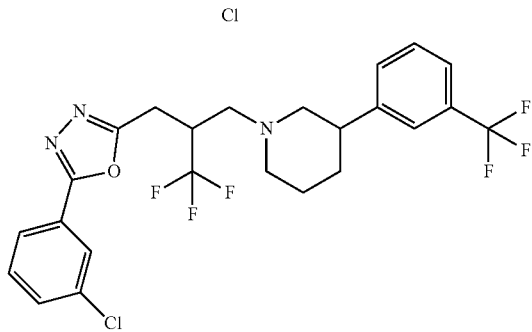 [SMILES: Cl ; FC(F)(F)c1cccc(C2CCCN(CC(Cc3nnc(-c4cccc(Cl)c4)o3)C(F)(F)F)C2)c1]

Prepared by a similar procedure to example 3 except substituting 3-chlorobenzohydrazide for 4-chlorobenzohydrazide afforded 32 mg of 1-{2-[5-(3-chloro-phenyl)-[1,3,4]oxadiazol-2-ylmethyl]-3,3,3-trifluoro-propyl}-3-(3-trifluoromethyl-phenyl)-piperidine hydrochloride as a white solid. LCMS MH+=518.

Example 10

2-Methyl-5-(5-{3,3,3-trifluoro-2-[3-(3-trifluoromethyl-phenyl)-piperidin-1-ylmethyl]-propyl}-[1,3,4]oxadiazol-2-yl)-pyridine

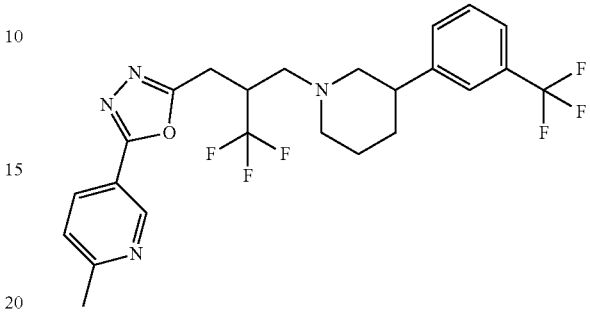

To a round-bottomed flask (5 ml) was added 4,4,4-trifluoro-3-((3-(3-(trifluoromethyl)phenyl)-piperidin-1-yl)methyl)butanoic acid (60 mg, 157 µmol), 6-methylnicotinohydrazide (23.7 mg, 157 µmol) and POCl$_3$ (1.64 g, 1 mL, 10.7 mmol). The reaction mixture was heated to reflux at 110° C. for 4 hr. The crude reaction mixture was allowed to cool to room temperature, poured into ice/water and made basic with a saturated solution of Na$_2$CO$_3$. The reaction mixture was extracted with ethyl acetate, washed with brine and H$_2$O, dried over MgSO$_4$, filtered and concentrated. The resultant residue was purified on a silica column (100% hexane to 60% ethyl acetate/hexane gradient) to afford 12 mg (15%) of 2-methyl-5-(5-{3,3,3-trifluoro-2-[3-(3-trifluoromethyl-phenyl)-piperidin-1-ylmethyl]-propyl}-[1,3,4]oxadiazol-2-yl)-pyridine as an off-white solid. MH+=499.

Example 11

5-Chloro-2-(5-{3,3,3-trifluoro-2-[3-(3-trifluoromethyl-phenyl)-piperidin-1-ylmethyl]-propyl}-[1,3,4]oxadiazol-2-yl)-pyridine hydrochloride

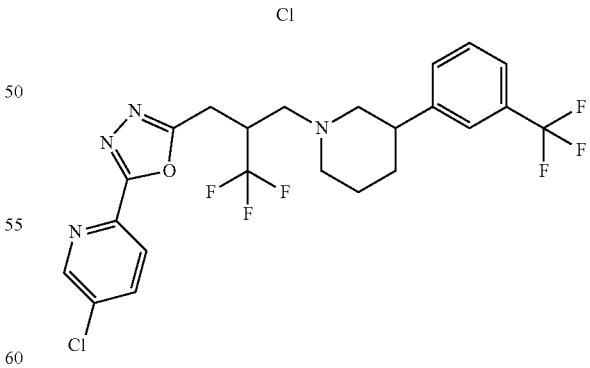

Prepared by a similar procedure to example 3 except substituting 5-chloropicolinohydrazide for 4-chlorobenzohydrazide afforded 12 mg of 5-chloro-2-(5-{3,3,3-trifluoro-2-[3-(3-trifluoromethyl-phenyl)-piperidin-1-ylmethyl]-propyl}-[1,3,4]oxadiazol-2-yl)-pyridine hydrochloride as a yellow solid. LCMS MH+=519.

Example 12

4-{3,3,3-Trifluoro-2-[5-(4-fluoro-phenyl)-[1,3,4]oxadiazol-2-ylmethyl]-propyl}-2-(3-trifluoromethyl-phenyl)-morpholine hydrochloride

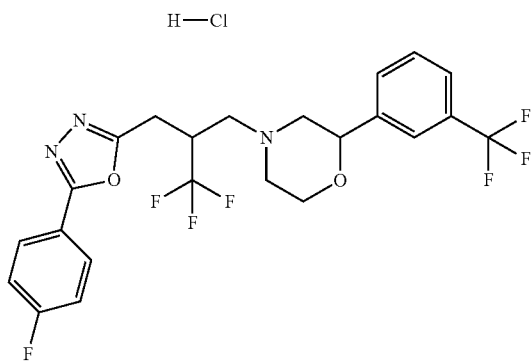 [SMILES: Cl ; Fc1ccc(-c2nnc(CC(CN3CCOC(c4cccc(C(F)(F)F)c4)C3)C(F)(F)F)o2)cc1]

To a 5 mL round-bottomed flask was added 4,4,4-trifluoro-3-((2-(3-(trifluoromethyl)phenyl)-morpholinomethyl)butanoic acid hydrochloride (100 mg, 260 μmol), 4-fluorobenzohydrazide (40.0 mg, 260 μmol) and POCl₃ (1.99 g, 1.21 ml, 13.0 mmol). The reaction mixture was heated at reflux (110° C.) for 4 hr. The crude reaction mixture was allowed to cool to room temperature, poured into ice/water and made basic with a saturated Na₂CO₃ solution. The resulting mixture was extracted with ethyl acetate. The organic phase was washed with brine and H₂O, dried over MgSO₄, filtered and concentrated. The crude material was purified by flash chromatography (silica gel, 12 g, 0% to 40% ethyl acetate in CH₂Cl₂/hexane (1:1) to afford 4-{3,3,3-trifluoro-2-[5-(4-fluoro-phenyl)-[1,3,4]oxadiazol-2-ylmethyl]-propyl}-2-(3-trifluoromethyl-phenyl)morpholine as an oil (93 mg, 67%). 4-{3,3,3-Trifluoro-2-[5-(4-fluoro-phenyl)-[1,3,4]oxadiazol-2-ylmethyl]-propyl}-2-(3-trifluoromethyl-phenyl)morpholine (45 mg) was dissolved in ether/hexane, treated with 4N HCl in dioxane (0.2 ml) and concentrated to afford 48 mg of 4-{3,3,3-trifluoro-2-[5-(4-fluoro-phenyl)-[1,3,4]oxadiazol-2-ylmethyl]-propyl}-2-(3-trifluoromethyl-phenyl)morpholine hydrochloride as a white solid. LCMS MH+=504.

Example 13

1-{2-[5-(4-Chloro-phenyl)-oxazol-2-ylmethyl]-3,3,3-trifluoro-propyl}-3-(3-trifluoromethyl-phenyl)-piperidine hydrochloride

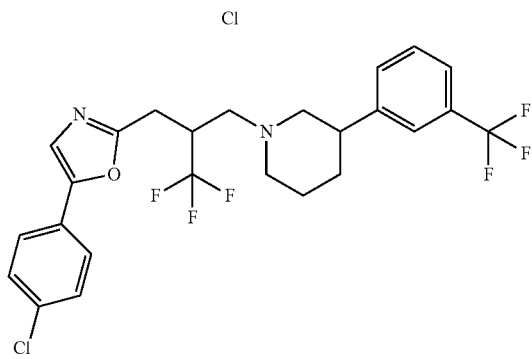 [SMILES: Cl ; FC(F)(F)c1cccc(C2CCCN(CC(Cc3ncc(-c4ccc(Cl)cc4)o3)C(F)(F)F)C2)c1]

4,4,4-Trifluoro-3-((3-(3-(trifluoromethyl)phenyl)piperidin-1-yl)methyl)butanoic acid was prepared by a similar procedure to Intermediate A except substituting 3-(3-trifluoromethylphenyl)-piperidine for 2-(3-(trifluoromethyl)phenyl)morpholine in step 1.

In a 10 mL pear-shaped flask, 4,4,4-trifluoro-3-((3-(3-(trifluoromethyl)phenyl)piperidin-1-yl)methyl)butanoic acid (40 mg, 104 μmol) and HATU (39.7 mg, 104 μmol) were combined with DMF (1 ml) to give a colorless solution. After 5 min of stirring, 2-amino-1-(4-chlorophenyl)ethanone HCl (21.5 mg, 104 μmol) was added followed by drop-wise addition of DIEA (47.2 mg, 63.8 μl, 365 μmol). The reaction mixture was stirred at room temperature overnight. The reaction mixture was diluted with ethyl acetate (30 ml), washed with brine and H₂O, dried over MgSO₄, filtered and concentrated in vacuo to give an oil. The crude material was purified by flash chromatography (silica gel, 12 g, 0% to 50% ethyl acetate in CH₂Cl₂) to afford 36 mg (65%) of N-(2-(4-chlorophenyl)-2-oxoethyl)-4,4,4-trifluoro-3-((3-(3-(trifluoromethyl)phenyl)piperidin-1-yl)methyl)butanamide as an oil. MH+=535.

In a 5 mL round-bottomed flask, N-(2-(4-chlorophenyl)-2-oxoethyl)-4,4,4-trifluoro-3-((3-(3-(trifluoromethyl)phenyl)piperidin-1-yl)methyl)butanamide (30 mg, 56.1 μmol) and POCl₃ (51.6 mg, 336 μmol) were combined with toluene (1 ml) to give a colorless solution. The reaction mixture was heated to 100° C. and stirred for 4 h. The reaction mixture was diluted with ethyl acetate (30 ml), poured into ice-water and made basic with saturated solution of Na₂CO₃. The organic layer was separated and washed with brine and H₂O, dried over MgSO₄, filtered and concentrated in vacuo to give an oil. The resultant oil was purified by flash chromatography (silica gel, 12 g, 0% to 50% ethyl acetate in hexane gradient) to afford 1-{2-[5-(4-chloro-phenyl)-oxazol-2-ylmethyl]-3,3,3-trifluoro-propyl}-3-(3-trifluoromethyl-phenyl)-piperidine as an oil. It was dissolved in Et₂O/Hexane, treated with 4N HCl in dioxane (0.1 ml) and concentrated in vacuo to afford 23 mg (76%) of 1-{2-[5-(4-chloro-phenyl)-oxazol-2-ylmethyl]-3,3,3-trifluoro-propyl}-3-(3-trifluoromethyl-phenyl)-piperidine hydrochloride as a white solid. MH+=517.

Example 14

1-{2-[3-(4-Chlorophenyl)-[1,2,4]oxadiazol-5-ylmethyl]-3,3,3-trifluoro-propyl}-3-(3-trifluoromethyl-phenyl)-piperidine hydrochloride

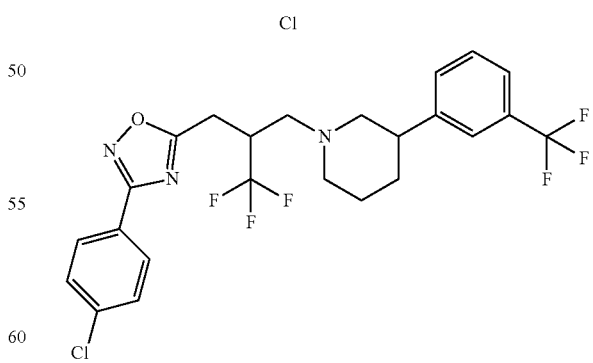

Step 1

In a 100 mL round-bottomed flask, 4-chlorobenzonitrile (2 g, 14.5 mmol) and hydroxylamine hydrochloride (1.00 g, 14.5 mmol) were combined with EtOH (20 ml) to give a colorless solution. DIEA (2.82 g, 3.81 ml, 21.8 mmol) was added and the reaction mixture was heated at 100° C. and stirred for 6 h. The crude reaction mixture was diluted with ethyl acetate (100 ml) and filtered. The solid was collected, washed with ethyl acetate and dried to afford 1.6 g (64%) of 4-chloro-N'-hydroxybenzimidamide as a white solid.

Step 2

In a 10 mL round-bottomed flask, 4,4,4-trifluoro-3-((3-(3-(trifluoromethyl)phenyl)piperidin-1-yl)methyl)butanoic acid (27 mg, 70.4 μmol) and HATU (26.8 mg, 70.4 μmol) were combined with DMF (1 ml) to give a colorless solution. DIEA (27.3 mg, 36.9 μl, 211 μmol) was added and the resulting mixture was stirred at room temperature for 10 min. 4-Chloro-N'-hydroxybenzimidamide (12.0 mg, 70.4 μmol) was added and the resulting mixture was stirred at room temperature for 4 hr. The reaction mixture was poured into 50 mL saturated NaCl/H$_2$O (1:1) and extracted with ethyl acetate (2×25 mL). The organic layers were combined, washed with saturated NaCl (1×20 mL), H$_2$O (2×50 mL), dried over MgSO$_4$, filtered and concentrated in vacuo to give N-((4-chlorophenyl)-(hydroxyimino)methyl)-4,4,4-trifluoro-3-((3-(3-(trifluoromethyl)phenyl)piperidin-1-yl)methyl)butanamide as an oil, which was used as is for the next reaction.

Step 3

In a 5 mL sealed tube, N-((4-chlorophenyl)(hydroxyimino)methyl)-4,4,4-trifluoro-3-((3-(3-(trifluoromethyl)phenyl)piperidin-1-yl)methyl)butanamide (30 mg, 56.0 μmol) was combined with DMF (2 ml) and heated at 120° C. for 3 hr. The reaction mixture was diluted with 30 ml of brine/water (1:1) and extracted with ether (2×30 ml). The combined organic layer was washed with brine and water, dried with MgSO$_4$, filtered and concentrated in vacuo to give an oil. This crude material was purified by flash chromatography (silica gel, 12 g, 0% to 30% ethyl acetate in hexanes gradient) to afford an oil. This oil was treated with 4NHCl in dioxane and hexane and concentrated to give 14 mg (41%) of 1-{2-[3-(4-chlorophenyl)-[1,2,4]oxadiazol-5-ylmethyl]-3,3,3-trifluoro-propyl}-3-(3-trifluoromethyl-phenyl)-piperidine hydrochloride as a viscous solid. This solid was a 1:1 mixture of diastereomers by LCMS (MS of each peak showed MH+=518).

Example 15

1-{3,3,3-Trifluoro-2-[5-(4-fluoro-phenyl)-[1,2,4]oxadiazol-3-ylmethyl]-propyl}-3-(3-trifluoromethyl-phenyl)-piperidine hydrochloride

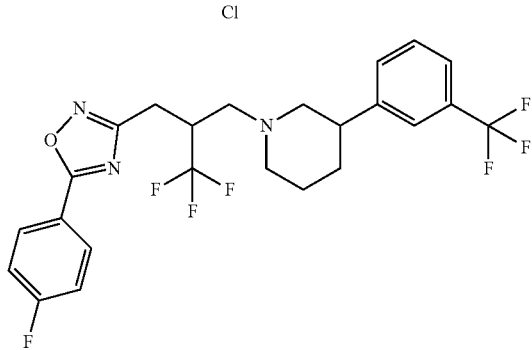 [SMILES: Cl ; Fc1ccc(-c2nc(CC(CN3CCCC(c4cccc(C(F)(F)F)c4)C3)C(F)(F)F)no2)cc1]

Step 1

In a 50 mL round-bottomed flask, 4,4,4-trifluoro-3-((3-(3-(trifluoromethyl)phenyl)piperidin-1-yl)methyl)butanenitrile (200 mg, 549 μmol) and hydroxylamine hydrochloride (37.9 mg, 549 μmol) were combined with EtOH (2 ml) to give a colorless suspension. DIEA (106 mg, 144 μl, 823 μmol) was added and the resulting mixture was stirred at 100° C. for 6 hr. The crude reaction mixture was concentrated in vacuo to give (Z)-4,4,4-trifluoro-N'-hydroxy-3-((3-(3-(trifluoromethyl)phenyl)-piperidin-1-yl)methyl)butanimidamide as a viscous oil. 85% pure by LC-MS. MH+=398.

Step 2

In a 10 mL round-bottomed flask, (Z)-4,4,4-trifluoro-N'-hydroxy-3-((3-(3-(trifluoromethyl)phenyl)-piperidin-1-yl)methyl)butanimidamide (120 mg, 302 μmol) and DIEA (117 mg, 158 μl, 906 μmol) were combined with CH$_2$Cl$_2$ (2.00 ml) to give a colorless solution. 4-Fluorobenzoyl chloride (47.9 mg, 302 μmol) in CH$_2$Cl$_2$ (1 ml) was added drop-wise and the resulting mixture was stirred at room temperature overnight. The crude reaction mixture was concentrated in vacuo to afford 120 mg (38%) of (Z)-4-fluoro-N-(4,4,4-trifluoro-1-(hydroxyimino)-3-((3-(3-(trifluoromethyl)phenyl)piperidin-1-yl)methyl)butyl)benzamide and used as is. MH+=520.

Step 3

In a 10 mL round-bottomed flask, (Z)-4-fluoro-N-(4,4,4-trifluoro-1-(hydroxyimino)-3-((3-(3-(trifluoromethyl)phenyl)piperidin-1-yl)methyl)butyl)benzamide (60 mg, 116 μmol) was combined with DMF (2 ml) to give a light yellow solution. The reaction mixture was heated at 120° C. and stirred for 4 h. The reaction mixture was diluted with ethyl acetate (30 ml), washed with brine (20 ml) and H$_2$O (2×50 ml), dried over MgSO$_4$, filtered and concentrated in vacuo. The crude material was purified by flash chromatography (silica gel, 12 g, 0% to 40% ethyl acetate in hexanes gradient) to afford an oil. This oil was dissolved in ether/hexane, treated with 4N HCl in dioxane (0.2 ml) and concentrated to afford 48 mg (79%) of 1-{3,3,3-trifluoro-2-[5-(4-fluorophenyl)-[1,2,4]oxadiazol-3-ylmethyl]-propyl}-3-(3-trifluoromethyl-phenyl)piperidine hydrochloride as a white solid.

Example 16

4-{2-[5-(4-Chlorophenyl)-[1,3,4]oxadiazol-2-ylmethyl]-3,3,3-trifluoropropyl}-2-(3-trifluoromethyl-phenyl)-morpholine hydrochloride

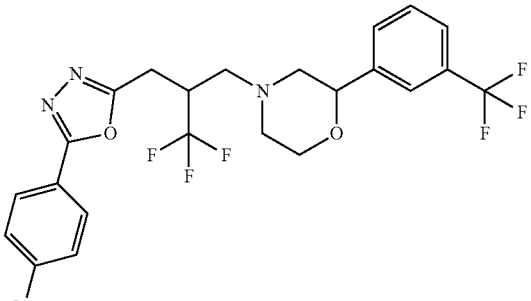

Prepared by a similar procedure to example 12 except substituting 4-chlorobenzohydrazide for 4-fluorobenzohydrazide afforded 23 mg (54%) of 4-{2-[5-(4-chlorophenyl)-[1,3,4]oxadiazol-2-ylmethyl]-3,3,3-trifluoropropyl}-2-(3-trifluoromethyl-phenyl)-morpholine hydrochloride as a white solid. LCMS MH+=520.

Example 17

4-{3,3,3-Trifluoro-2-[5-(4-fluoro-phenyl)-[1,3,4]oxadiazol-2-ylmethyl]-propyl}-2-(4-trifluoromethyl-phenyl)-morpholine hydrochloride 4,4,4-Trifluoro-3-((2-(4-(trifluoromethyl)phenyl)morpholino)methyl)butanoic acid was prepared by a similar procedure to Intermediate A except substituting 2-(4-trifluoromethyl-phenyl)-morpholine for 2-(3-(trifluoromethyl)phenyl) morpholine in step 1.

To a round-bottomed flask (5 ml) was added 4,4,4-trifluoro-3-((2-(4-(trifluoromethyl)phenyl)-morpholino)methyl)butanoic acid (50 mg, 130 μmol), 4-fluorobenzohydrazide (20.0 mg, 130 μmol) and POCl₃ (995 mg, 605 μl, 6.49 mmol). The reaction mixture was heated at reflux (110° C.) for 4 h. The crude reaction mixture was allowed to cool to room temperature, poured into ice/water and made basic with a saturated solution of Na₂CO₃. The reaction mixture was extracted with ethyl acetate, washed with brine and H₂O, dried over MgSO₄, filtered and concentrated. The crude material was purified by flash chromatography (silica gel, 12 g, 0% to 40% ethyl acetate/hexane gradient) to give an oil (28 mg). The oil was dissolved in ether/hexane, treated with 4N HCl in dioxane (0.2 ml) and concentrated to afford 26 mg (38%) of 4-{3,3,3-trifluoro-2-[5-(4-fluoro-phenyl)-[1,3,4]oxadiazol-2-ylmethyl]-propyl}-2-(4-trifluoromethyl-phenyl)-morpholine hydrochloride a white solid. MH+=504.

Example 18

4-{2-[5-(4-Chloro-phenyl)-[1,3,4]oxadiazol-2-ylmethyl]-3,3,3-trifluoro-propyl}-2-(4-trifluoromethyl-phenyl)-morpholinehydrochloride Prepared by a similar procedure to example 17 except substituting 4-chlorobenzohydrazide for 4-fluorobenzohydrazide afforded 24 mg (34%) of 4-{2-[5-(4-chloro-phenyl)-[1,3,4]oxadiazol-2-ylmethyl]-3,3,3-trifluoro-propyl}-2-(4-trifluoromethyl-phenyl)-morpholinehydrochloride as a white solid. LCMS MH+=520.

Example 19

IC₅₀ Determination of Exemplified Compounds
Dose Response Assay: ChanTest hTRPA1-CHO
Stably Transfected Cell Line Cell Culture and Assay Reagents:

| | |
|---|---|
| Ham's F12 | (GIBCO #11765-047) |
| Tetracycline-free Fetal Bovine Serum | (ClonTech#631106, Lot A301097018) |
| Blasticidin (10 mg/ml stock) | (GIBCO #A11139-02) |
| Zeocin (100 mg/ml stock) | (GIBCO #R250-01) |
| Doxycycline | (SIGMA #D9891) |
| Penicillin-Spreptomycin solution (100X) | (GIBCO #15140-122) |
| GlutaMAX (100X) | (GIBCO #35050) |
| Trypsin-EDTA | (GIBCO #25200-056) |
| PBS (without Calcium and Magnesium) | (GIBCO #14190) |
| HBSS | (GIBCO #14025) |
| Hepes | (GIBCO #15630) |
| BSA (fatty acid free, low endotoxin) | (SIGMA #A8806-5G) |
| DMSO | (SIGMA #D2650) |
| AP-18 | (SIGMA #A7232) |
| Cinnamaldehyde | (SIGMA #W228613) |
| ATP | (SIGMA #A-6419) |
| 2-Aminoethyl diphenylborinate | (SIGMA #D9754) |
| Menthol | (Sigma #M2772) |
| FLIPR Calcium 3 Assay Kit | (Molecular Devices #R8108) |
| Probenecid | (INVITROGEN #36400) |
| Plates | (BD #35-3962) |

CHO-K1 Tet-On HOMSA TRPA1 Clone 20
  Chinese Hamster Ovary cells, inducible expression
Clone #20, received at passage #26
Channel expression in this cell line has been shown to be stable for at least 80 passages
Verified Mycoplasma free with MycoAlert Kit
Cell line expanded and banked
Growth Conditions:
  Growth Media for CHO-K1 Tet-On_HOMSA_TRPA1_Clone_20
    Ham's F-12 with 10% tetracycline-free FBS
    1× penicillin-streptomycin
    1× glutamax
    0.01 mg/ml Blasticidin
    0.40 mg/ml Zeocin
    The cell line doubling rate was ~15 hours. The culture plates did not exceed 80% confluency.
    To induce expression, tetracycline was added to blasticidin/zeocin-free media at a final concentration of 1 ug/ml. Experiments were run at 24 hours post induction.
Plating Conditions CHOK1/TRPA1 Cells:
  Harvested cells with 0.025% trypsin/EDTA.
  Resuspended cells in growth media without selection antibiotics.
  Measured cell density and diluted to $2.4 \times 10^5$ cells/ml in media containing 1 ug/ml Doxycycline Plate 25 ul/well into 384 well black/clear tissue culture-treated plates.
  Incubated overnight at 37° C.
Calcium Flux Assay:
Day of Assay:
Reagents:
Replacement Buffer: Hank's Balanced Salt Solution, 20 mM HEPES along with 0.005% BSA and 2× Probenecid
Dye Loading Buffer: Cal-3 NW Calcium dye was prepared by dissolving the contents of one vial with 500 ml Hank's Balanced Salt Solution containing 20 mM HEPES.

Control Compounds for CHOK1/TRPA1 Cells:
AP-18, stock 10 mM, prepare 3.5× compound dilution in a
  Compound Buffer (HBSS/20 mM HEPES/0.005% BSA)–
  final concentration 10 uM.
Preparation of Cinnamaldehyde (Agonist Addition):
FW=132.16
  Specific gravity=1.046 gm/cc
  1.32 gm/1.046 gm/cc=1.26 ml of stock
  Add 1.74 ml DMSO=3.3 M stock
  Working solution 4.5× (final 100 uM in Compound Buffer:
    HBSS/20 mM HEPES/0.005% BSA)
Compounds dilutions were prepared from 5 or 10 mM
stock (100% DMSO):
  Adjustments of volumes and concentrations were made at
    time of titration to reflect desired final assay concentrations.
  Compounds were tested at either 20 μM three folds dilution
    11 steps out or 30 μM two folds dilution 11 steps out.
  3 μl of diluted compound were transferred into Weidmann
    384-well plate in duplicates side-by-side.
  Compound plates were resuspended with 100 ul of HBSS/
    20 mM HEPES/0.005% BSA buffer (Compound
    Buffer):
  column 1A-H: buffer/DMSO (bk)
  column 2A-H: AP-18 (control antagonist for CHOK1
    TRPA1 cells)
  column 1I-P: ATP (control for CHOK1 teton cells)
  column 2I-P: 2APB (control antagonist for CHOK1/
    TRPM8 cells).
Growth media was removed from the cell plates (20 ul) and
20 ul of the Replacement Buffer was added followed by
addition of 25 ul of diluted dye. All three steps were performed using a Plate Washer BioTek 407. The plates were
then incubated for 30' at RT.
After incubation, both the cell and compound plates were
brought to the FLIPR and 20 ul of the diluted compounds/
antagonist/bk were transferred to the cell plates by the FLIPR.
Plates were then incubated for 30' at room temperature. After
30' incubation, plates were returned to the FLIPR and 20 ul of
4.5× Cinnamaldehyde was added to the cell plates. During the
compound addition as well as agonist addition, fluorescence
readings were taken simultaneously from all 384 wells of the
cell plate every 1.5 seconds. Five readings were taken to
establish a stable baseline, then 20 ul of sample was rapidly
(30 ul/sec) and simultaneously added to each well of the cell
plate. The fluorescence was continuously monitored before,
during and after sample/agonist addition for a total elapsed
time of 100 seconds (compound addition) and 120 seconds
(agonist addition). Responses (increase in peak fluorescence)
in each well following agonist addition was determined. The
initial fluorescence reading from each well, prior to ligand
stimulation, was used a zero baseline value for the data from
that well. The responses were expressed as % inhibition of the
inhibitor control as shown in Table 1 below:

TABLE 1

| Example No. | hTRPA1; IC50 uM |
| --- | --- |
| 1 | 6.7215 |
| 2 | 3.7 |
| 3 | 0.702 |
| 4 | 12.31433 |
| 5 | 11.1615 |
| 6 | 2.261667 |
| 7 | 6.045667 |
| 8 | 0.115667 |

TABLE 1-continued

| Example No. | hTRPA1; IC50 uM |
| --- | --- |
| 9 | 9.1055 |
| 10 | 2.398 |
| 11 | 30 |
| 12 | 0.1123 |
| 13 | 7.2685 |
| 14 | 2.66 |
| 15 | 0.318 |
| 16 | 0.2275 |
| 17 | 0.0621 |
| 18 | 0.2665 |

It is to be understood that the invention is not limited to the particular embodiments of the invention described above, as variations of the particular embodiments may be made and still fall within the scope of the appended claims.

The invention claimed is:

1. A compound of formula (I):

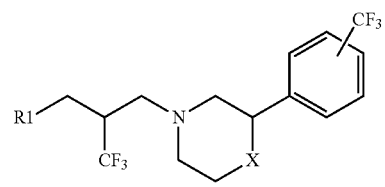

wherein:
  X is —CH$_2$— or oxygen; and
  R1 is benzoimidazolyl, benzimidazole ring substituted with a halogen, benzooxazolyl, benzoxazole ring substituted with a halogen, an unsubstituted 5-membered heteroaryl ring or a 5-membered heteroaryl ring substituted with halo-phenyl, methyl-pyridinyl or halo-pyridinyl, or a pharmaceutically acceptable salt thereof.

2. The compound according to claim 1, wherein X is —CH$_2$—.

3. The compound according to claim 1, wherein said 5-membered heteroaryl ring is imidazolyl, oxazolyl or oxadiazolyl.

4. The compound according to claim 1, wherein said halo moiety is fluorine or chlorine.

5. The compound according to claim 1, wherein said compound is:
  5-Chloro-2-{3,3,3-trifluoro-2-[3-(3-trifluoromethylphenyl)-piperidin-1-ylmethyl]-propyl}-1H-benzoimidazole hydrochloride;
  1-{2-[5-(4-Chlorophenyl)-1H-imidazol-2-ylmethyl]-3,3,3-trifluoropropyl}-3-(3-trifluoromethyl-phenyl)piperidine hydrochloride;
  1-{2-[5-(4-Chlorophenyl)-[1,3,4]oxadiazol-2-ylmethyl]-3,3,3-trifluoropropyl}-3-(3-trifluoromethylphenyl)-piperidine hydrochloride;
  6-Chloro-2-{3,3,3-trifluoro-2-[3-(3-trifluoromethylphenyl)-piperidin-1-ylmethyl]-propyl}-benzooxazole hydrochloride;
  3-(3-Trifluoromethylphenyl)-1-[3,3,3-trifluoro-2-(5-phenyl-1H-imidazol-2-ylmethyl)-propyl]-piperidine hydrochloride;
  1-{2-[5-(3-Chlorophenyl)-1H-imidazol-2-ylmethyl]-3,3,3-trifluoropropyl}-3-(3-trifluoromethyl-phenyl)piperidine hydrochloride;

1-{3,3,3-Trifluoro-2-[5-(4-fluorophenyl)-1H-imidazol-2-ylmethyl]-propyl}-3-(3-trifluoromethylphenyl)-piperidine hydrochloride;

1-{3,3,3-Trifluoro-2-[5-(4-fluorophenyl)-[1,3,4]oxadiazol-2-ylmethyl]-propyl}-3-(3-trifluoromethylphenyl)-piperidine hydrochloride;

1-{2-[5-(3-Chlorophenyl)-[1,3,4]oxadiazol-2-ylmethyl]-3,3,3-trifluoro-propyl}-3-(3-trifluoromethylphenyl)-piperidine hydrochloride;

2-Methyl-5-(5-{3,3,3-trifluoro-2-[3-(3-trifluoromethylphenyl)-piperidin-1-ylmethyl]-propyl}-[1,3,4]oxadiazol-2-yl)-pyridine;

5-Chloro-2-(5-{3,3,3-trifluoro-2-[3-(3-trifluoromethylphenyl)-piperidin-1-ylmethyl]-propyl}-[1,3,4]oxadiazol-2-yl)-pyridine hydrochloride;

4-{3,3,3-Trifluoro-2-[5-(4-fluoro-phenyl)-[1,3,4]oxadiazol-2-ylmethyl]-propyl}-2-(3-trifluoromethylphenyl)-morpholine hydrochloride;

1-{2-[5-(4-Chlorophenyl)-oxazol-2-ylmethyl]-3,3,3-trifluoro-propyl}-3-(3-trifluoromethyl-phenyl)-piperidine hydrochloride;

1-{2-[3-(4-Chlorophenyl)-[1,2,4]oxadiazol-5-ylmethyl]-3,3,3-trifluoropropyl}-3-(3-trifluoromethylphenyl)-piperidine hydrochloride;

1-{3,3,3-Trifluoro-2-[5-(4-fluoro-phenyl)-[1,2,4]oxadiazol-3-ylmethyl]-propyl}-3-(3-trifluoromethylphenyl)-piperidine hydrochloride;

4-{2-[5-(4-Chlorophenyl)-[1,3,4]oxadiazol-2-ylmethyl]-3,3,3-trifluoropropyl}-2-(3-trifluoromethylphenyl)-morpholine hydrochloride;

4-{3,3,3-Trifluoro-2-[5-(4-fluorophenyl)-[1,3,4]oxadiazol-2-ylmethyl]-propyl}-2-(4-trifluoromethylphenyl)-morpholine hydrochloride; or 4-{2-[5-(4-Chlorophenyl)-[1,3,4]oxadiazol-2-ylmethyl]-3,3,3-trifluoropropyl}-2-(4-trifluoromethylphenyl)-morpholinehydrochloride.

6. A pharmaceutical composition, comprising a therapeutically effective amount of a compound according to claim 1 and a pharmaceutically acceptable carrier.

7. A method of treating a respiratory disorder mediated by TRPA1, the method comprising administering a therapeutically effective amount of a compound according to claim 1 to a subject in need thereof.

8. The method of claim 7, wherein the respiratory disorder is selected from the group consisting of chronic obstructive pulmonary disorder (COPD), asthma, allergic rhinitis, and bronchospasm.

* * * * *